(12) United States Patent
Albrechtsen et al.

(10) Patent No.: US 8,585,677 B2
(45) Date of Patent: Nov. 19, 2013

(54) LAMINAR INJECTION APPARATUS AND METHOD

(75) Inventors: Nathan B. Albrechtsen, Provo, UT (US); Larry L. Howell, Orem, UT (US); Spencer P. Magleby, Provo, UT (US)

(73) Assignee: Brigham Young University, Provo, UT (US)

( * ) Notice: Subject to any disclaimer, the term of this patent is extended or adjusted under 35 U.S.C. 154(b) by 12 days.

(21) Appl. No.: 13/239,302

(22) Filed: Sep. 21, 2011

(65) Prior Publication Data

US 2012/0245557 A1 Sep. 27, 2012

Related U.S. Application Data

(60) Provisional application No. 61/403,758, filed on Sep. 21, 2010.

(51) Int. Cl.
*A61M 31/00* (2006.01)
*A61M 5/00* (2006.01)
*A61M 5/32* (2006.01)

(52) U.S. Cl.
USPC ............ 604/506; 604/187; 604/216; 604/192

(58) Field of Classification Search
USPC ..................... 604/506, 187, 216, 192, 500
See application file for complete search history.

(56) References Cited

U.S. PATENT DOCUMENTS

| | | | |
|---|---|---|---|
| 4,340,048 A | 7/1982 | Eckenhoff | |
| 4,886,499 A | 12/1989 | Cirelli et al. | |
| 5,527,288 A | 6/1996 | Gross et al. | |
| 5,814,020 A | 9/1998 | Gross | |
| 5,858,001 A | 1/1999 | Tsals et al. | |
| 5,931,814 A | 8/1999 | Alex et al. | |
| 5,957,895 A | 9/1999 | Sage et al. | |
| 5,997,501 A | 12/1999 | Gross et al. | |
| 6,979,316 B1 | 12/2005 | Rubin et al. | |
| 6,983,924 B2 | 1/2006 | Howell et al. | |
| 7,628,770 B2 | 12/2009 | Ethelfeld | |
| 2003/0236502 A1 | 12/2003 | De La Serna | |
| 2006/0247579 A1* | 11/2006 | Friedman | 604/197 |
| 2008/0039794 A1* | 2/2008 | Kornerup et al. | 604/136 |
| 2009/0082727 A1 | 3/2009 | Moeller et al. | |
| 2010/0278785 A1 | 11/2010 | Schwaiger et al. | |

* cited by examiner

*Primary Examiner* — Kevin C Sirmons
*Assistant Examiner* — Imani Hayman
(74) *Attorney, Agent, or Firm* — Utah Valley Patent; Steve McDaniel

(57) ABSTRACT

A laminar injection apparatus may include a slider layer, a needle flexibly coupled to the slider layer, a medication reservoir in fluid communication with the needle, and a needle guiding layer comprising an aperture for deflecting the needle from a substantially horizontal orientation to a substantially vertical orientation in response to moving the slider layer relative to the needle guiding layer. One or more spring layers may extend the laminar structure into an extended laminar structure. The needle may be thrust into a subject by compressing the extended laminar structure and causing the needle to protrude from the structure and penetrate a subject. In response to the compressive force on the laminar stack, medication may be forced from the medication reservoir through the needle and into the subject.

17 Claims, 4 Drawing Sheets

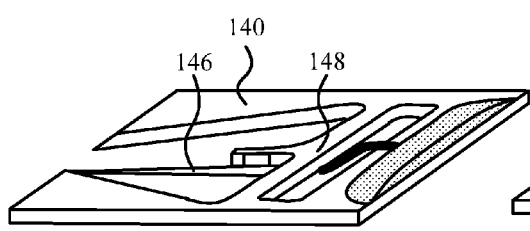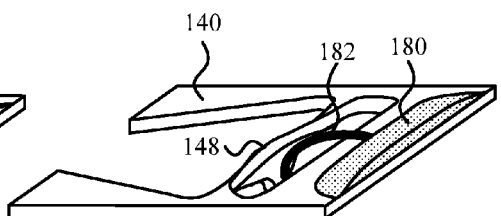
Fig. 2a  Fig. 2b
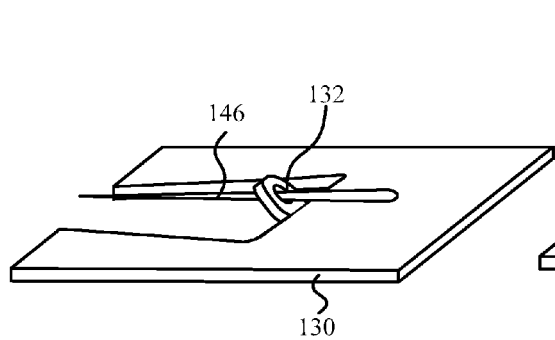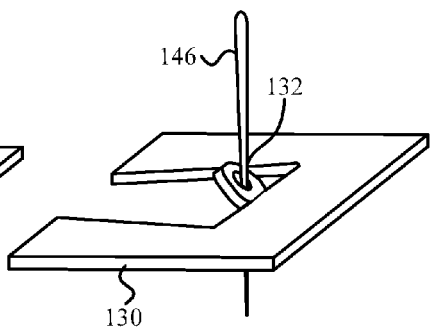
Fig. 3a  Fig. 3b

LAMINAR INJECTION APPARATUS AND METHOD

RELATED APPLICATIONS

This application claims priority to U.S. Provisional Patent Application No. 61/403,758 entitled "Method and Apparatus of Lancing a Credit-card-sized Injector" and filed on 21 Sep. 2010 for Nathan B. Albrechtsen, Larry L. Howell, and Spencer P. Magleby. The aforementioned application is incorporated herein by reference in its entirety.

BACKGROUND OF THE INVENTION

1. Field of the Invention

This invention relates generally to Lamina Emergent Mechanisms (LEMs) and more particularly relates to apparatii and methods for injecting medications using LEMs.

2. Description of the Related Art

LEMs are typically defined by three functional characteristics: they are compliant (i.e. flexible), fabricated from planar materials, and emerge into a 3-D structure from a flat initial state. Due to their laminar nature, they are typically very compact and cost effective to manufacture. Providing a medication injection apparatus and method using LEMs would therefore provide advantages that are lacking in currently available medication injection aparatii and methods.

SUMMARY OF THE INVENTION

The present invention has been developed in response to the present state of the art, and in particular, in response to the problems and needs in the art that have not yet been fully solved by currently available medication injection devices and methods. Accordingly, the present invention has been developed to provide an apparatus and method for injecting medications that overcome many of the shortcomings in the art.

As detailed below, an apparatus for injecting medications may be a laminar structure that includes a slider layer, a needle flexibly coupled to the slider layer, a medication reservoir in fluid communication with the needle, and a needle guiding layer that deflects the needle from a substantially horizontal orientation to a substantially vertical orientation in response to moving the slider layer relative to the needle guiding layer. One or more spring layers may extend the laminar structure into an extended laminar structure. The needle may be thrust into a subject by compressing the extended laminar structure and causing the needle to protrude from the structure and penetrate a subject. In response to the compressive force on the laminar stack, medication may be forced from the medication reservoir through the needle and into the subject.

The present invention provides a variety of advantages. It should be noted that references to features, advantages, or similar language within this specification does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

The aforementioned features and advantages of the present invention will become more fully apparent from the following description and appended claims, or may be learned by the practice of the invention as set forth hereinafter.

BRIEF DESCRIPTION OF THE DRAWINGS

To enable the advantages of the invention to be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIGS. 2a and 2b are detailed perspective view illustrations of one embodiment of a needle guiding layer of the present invention;

FIGS. 3a and 3b are detailed perspective view illustration of one embodiment of a sliding layer of the present invention;

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Figure 1:
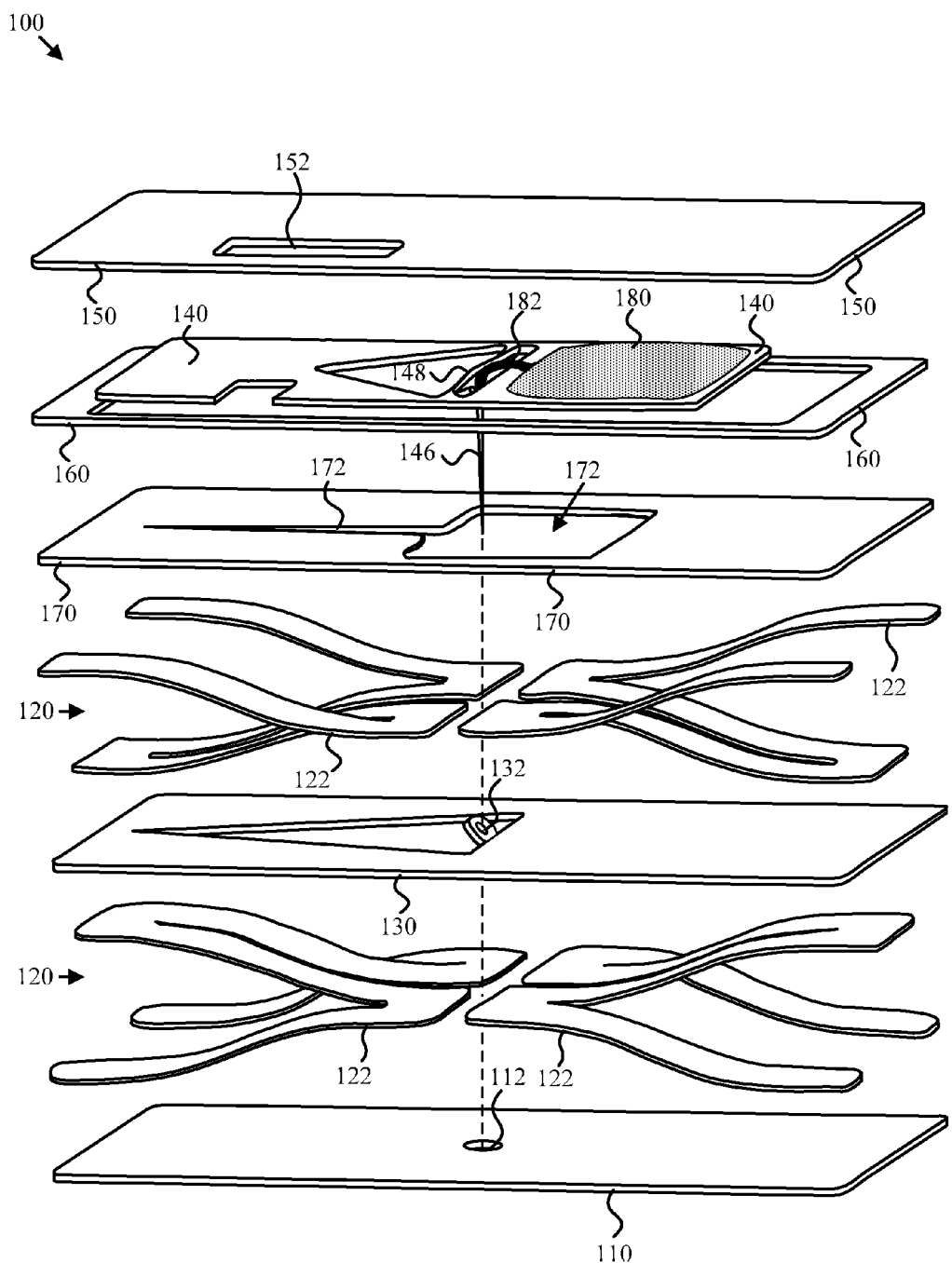
FIG. 1 is a exploded perspective view illustration of one embodiment of a medication injection apparatus of the present invention.

FIG. 1 is an exploded perspective view illustration of one embodiment of a medication injection apparatus 100 of the present invention. As depicted, the medication injection apparatus 100 includes a base plate 110 with a dispensing port 112, one or more spring layers 120, a needle guiding layer 130 with a guiding aperture 132, a slider layer 140, a top plate 150 with an access aperture 152, a perimeter spacer 160, a needle guard layer 170 and a medication reservoir 180. The medication injection apparatus 100 may be a Laminar Emergent Mechanism that expands from a flattened laminar structure to an extended compressible structure.

The base plate may have a dispensing port 112 through which a needle 146 may pass. The base plate 110 and the top plate 150 may cover the bottom and top of the laminar structure when in a flattened state. The laminar structure may be held in a flattened state by a variety of mechanisms (not shown) including a sleeve, a band, a clip and external packaging such as a plastic wrap. In other embodiments, an internal release structure (not shown) may be integrated into the laminar structure which is activated by moving the slider layer 140 relative to the needle guiding layer 130.

Each spring layer 120 may include one or more emergent beam springs 122. In certain embodiments, upon release of the base plate 110 from the top plate 150, the spring layers 120 may automatically extend the laminar structure and cause a needle 146 to rotate (via the guiding aperture 132) and cause the slider layer 140 to move relative to the needle guiding layer 130. The movement may include lateral and vertical components. In other embodiments, a user moves the slider layer 140 relative to the needle guiding layer via the access aperture 152 and thereby causes rotation of the needle 146 from a substantially horizontal orientation to a substantially vertical orientation and extension of the laminar structure 100. In either case, the extended height of the laminar structure may be sufficient to keep the needle 146 from protruding from the extended laminar structure (see FIG. 5b).

In the depicted embodiment, the guiding aperture 132 is angled to facilitate deflection of the needle 146 from a substantially horizontal orientation (i.e. substantially parallel to the slider layer 140) to a substantially vertical orientation (i.e. substantially perpendicular to the slider layer 140) in response to moving the slider layer relative to the needle guiding layer 130.

The perimeter spacer 160 may surround the sliding layer 140. In one embodiment, the perimeter spacer 160 is bonded to the top plate 150 and the needle guard layer 170 and thereby provides a channel of movement for the slider layer 140 and the medication reservoir 180. The perimeter spacer may be thicker than the slider layer 140 and/or the medication reservoir 180 in order to facilitate movement of the slider layer 140.

The needle guard layer 170 may provide a cavity 172 which houses the needle 146 while the apparatus 100 is in a flattened state and enables a torsion hinge 148 to twist as the needle 146 is deflected (i.e. rotated) from a substantially horizontal orientation to a substantially vertical orientation.

The depicted medication reservoir 180 is a pouch or a bag which is bonded to the slider layer 140 and connected to the needle 146 via a connection tube 182. In the depicted embodiment, the pouch covers a portion of the slider layer 140. In another embodiment, the pouch substantially fills the volume above the slider layer 140 created by the perimeter spacer 160 and may be bonded to the top plate 150 in addition to the slider layer 140. In addition to a pouch or a bag, the medication reservoir 180 may also be a compressible tube with closed ends, a bellows, or any chamber suitable to hold and dispense medication. The medication reservoir 180 may also be integral to one of the laminar layers such as the slider layer 140.

In certain embodiments a wiping element (not shown) is used to push medication from the medication reservoir 180 via a peristaltic motion. In some embodiments, the wiping element is a separate layer in the laminar stack. In other embodiments, the wiping element is a ridge on one of the layers such as the top layer. The wiping element may be actuated directly by the user, via the emergent motion of the laminar injector, or via compression of the extended laminar device by the user.

FIGS. 2a and 2b are detailed perspective view illustrations of one embodiment of the needle guiding layer 130. Similarly, FIGS. 3a and 3b are detailed perspective view illustrations of one embodiment of the slider layer 140. FIGS. 2a and 3a correspond to a flattened state for the laminar structure 100, while FIGS. 2b and 3b correspond to an extended state for the laminar structure 100. The transition from the flattened state to the extended state of the laminar structure may correspond to movement of the slider layer 140 relative to the needle guiding layer 130.

Figure 4:
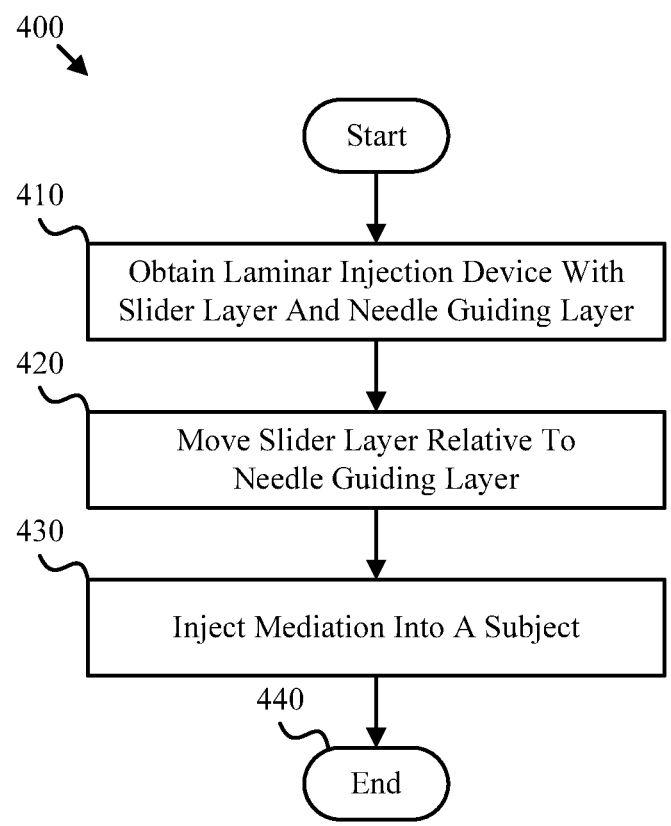
FIG. 4 is a flowchart diagram of one embodiment of a medication injection method of the present invention.

FIG. 4 is a flowchart diagram of one embodiment of a medication injection method 400 of the present invention. As depicted, the medication injection method 400 includes obtaining 410 a laminar injection device, moving 420 a slider layer, and injecting 430 medication into a subject. The depicted method may be conducted in conjunction with the medication injection apparatus 100 or the like.

Obtaining 410 a laminar injection device may include obtaining a device comprising a slider layer, a needle flexibly coupled to the slider layer, a medication reservoir in fluid communication with the needle, and a needle guiding layer. The needle guiding layer may include an aperture for deflecting the needle from a substantially horizontal orientation to a substantially vertical orientation in response to moving the slider layer relative to the needle guiding layer. In one embodiment, the obtained laminar injection device is the medication injection apparatus 100.

Subsequent to obtaining 410 a laminar injection device the method may be continued by moving 420 the slider layer relative to the needle guiding layer in order to move the needle from a substantially horizontal orientation to a substantially vertical orientation. In some embodiments, moving 420 the slider layer may also release a base plate from a top plate and vertically extend the laminar structure via one or more spring layers. In other embodiments, releasing the base plate from the top plate enables one or more spring layers to simultaneously extend the laminar structure and move the slider layer relative to the needle guiding layer. The vertical extension of the laminar structure may keep the needle for protruding from the injection apparatus until actual injection occurs. See FIG. 5b.

Injecting 430 medication from the medication reservoir may be initiated by compressing the extended laminar structure and causing the needle to protrude from the compressing laminar structure and thereby enable the needle to be thrust into a subject. In response to the compressive force on the laminar stack, medication may be forced from the medication reservoir, through the connecting tube and needle and into the subject.

One of skill in the art will appreciate the pressure necessary to force fluid from the medication reservoir and through the needle may be selected to correspond to a particular compression distance for the extended laminar stack and a particular (i.e. desired) injection depth for the needle. For example, the medication reservoir or outlet thereof may be fitted with a flexible member that functions as a one way valve and opens at a particular pressure level. Furthermore, the spring layers may be selected to have a stiffness coefficient that is consistent with the desired injection depth for the needle and the selected release pressure release for the medication reservoir.

In certain embodiments, the size of the laminar injection device is approximately that of a credit card which facilitates ready availability for individuals and facilitates responding to emergencies. The medication contained in the medication reservoir of the laminar injection device may be any useful liquid medication such as epinephrine, insulin, antihistamines, or seizure medication.

Figure 5A:
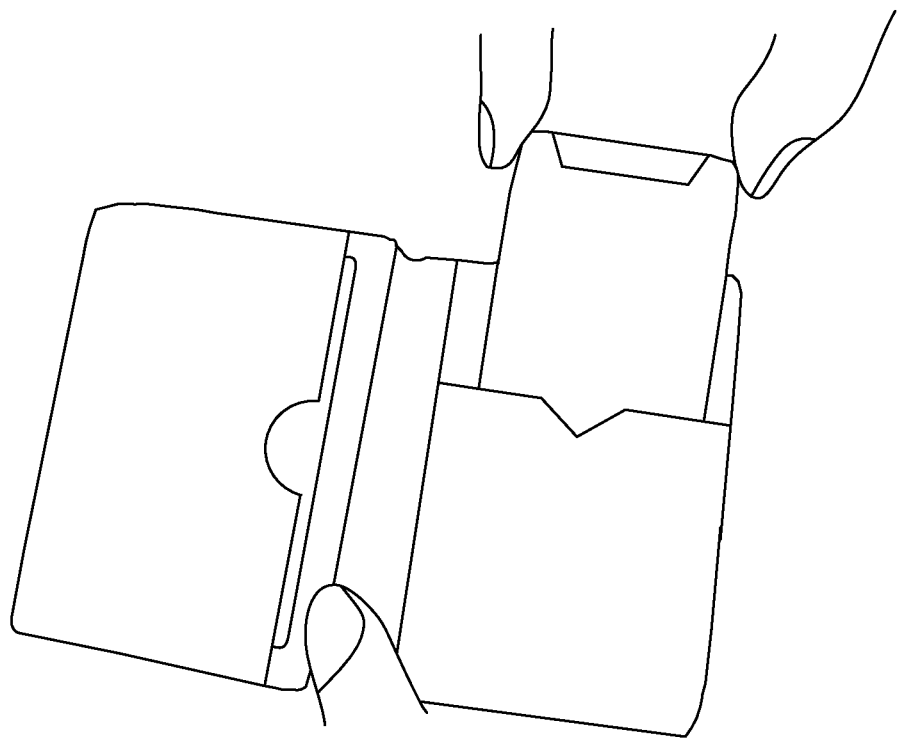
FIGS. 5a and 5b are perspective view illustrations depicting the deployment of one embodiment of a medication injection apparatus of the present invention.
Figure 5B:
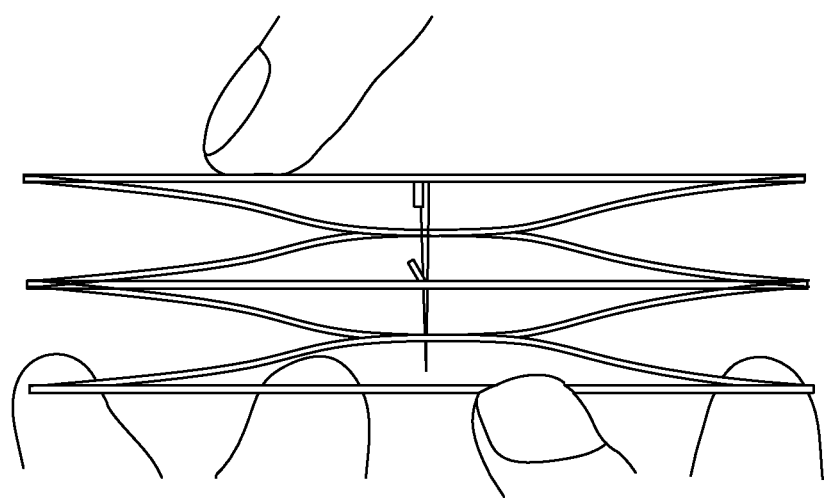

FIGS. 5a and 5b are perspective view photographs depicting the deployment of one embodiment of a medication injection apparatus of the present invention. FIG. 5a depicts a flattened state 510 where the top plate and base plate have not been released from each other. In contrast, FIG. 5b depicts an extended state 520 where the laminar stack is extended, the needle is in a substantially vertical orientation and ready for use as a medication injector.

The present invention provides improved medication injection devices and methods. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A laminar apparatus for injecting medication, the apparatus comprising:
   a slider layer;
   a needle flexibly coupled to the slider layer; and
   a needle guiding layer comprising an angled aperture for deflecting the needle from a substantially horizontal orientation that is substantially parallel to the slider layer to a substantially vertical orientation that is substantially perpendicular to the slider layer in response to moving the slider layer relative to the needle guiding layer.

2. The apparatus of claim 1, further comprising one or more spring layers, each spring layer thereof comprising at least one laminar emergent beam spring.

3. The apparatus of claim 2, wherein the spring layers are configured to automatically extend the slider layer away from the needle guiding layer and cause the needle guiding layer to deflect the needle from the substantially horizontal orientation to the substantially vertical orientation.

4. The apparatus of claim 1, wherein the slider layer comprises a torsional hinge for coupling the slider layer to the needle.

5. The apparatus of claim 1, further comprising a medication reservoir for holding and dispensing medication, the medication reservoir in fluid communication with the needle.

6. The apparatus of claim 5, wherein the medication reservoir is attached to, or integrated within, the slider layer.

7. The apparatus of claim 5, wherein the medication reservoir is selected from the group consisting of a pouch, a bag, a closed end tube and a bellows.

8. The apparatus of claim 1, wherein the lateral dimensions of the needle guiding layer are approximately those of a typical credit card.

9. The apparatus of claim 1, further comprising a needle guarding layer.

10. The apparatus of claim 9, further comprising a perimeter spacer that surrounds the perimeter of the slider layer.

11. The apparatus of claim 10, wherein the perimeter spacer is bonded to the needle guarding layer and the top plate.

12. The apparatus of claim 10, wherein the lateral dimensions of each layer is substantially equal to or less than that those of a typical credit card.

13. A method for injecting medication, the method comprising:
   obtaining a laminar apparatus for injecting medication, the apparatus comprising a slider layer, a needle flexibly coupled to the slider layer, a medication reservoir in fluid communication with the needle, and a needle guiding layer comprising an angled aperture for deflecting the needle from a substantially horizontal orientation that is substantially parallel to the slider layer to a substantially vertical orientation that is substantially perpendicular to the slider layer in response to moving at least a portion of the slider layer relative to the needle guiding layer;
   moving the slider layer relative to the needle guiding layer; and
   injecting medication from the medication reservoir into a subject via the needle.

14. The method of claim 13, wherein the medication is epinephrine.

15. The method of claim 13, wherein the medication is insulin.

16. The method of claim 13, wherein the medication is an antihistamine.

17. The method of claim 13, wherein the lateral dimensions of the needle guiding layer are approximately those of a typical credit card.

* * * * *